(12) United States Patent
Roberts et al.

(10) Patent No.: US 7,629,328 B2
(45) Date of Patent: Dec. 8, 2009

(54) NUCLEOSIDE DERIVATIVES FOR TREATING HEPATITIS C VIRUS INFECTION

(75) Inventors: Christopher D. Roberts, Belmont, CA (US); Jesse Keicher, Menlo Park, CA (US); Natalia B. Dyatkina, Mountain View, CA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 12/206,581

(22) Filed: Sep. 8, 2008

(65) Prior Publication Data

US 2009/0036399 A1 Feb. 5, 2009

Related U.S. Application Data

(63) Continuation of application No. 11/492,558, filed on Jul. 24, 2006, now Pat. No. 7,432,248, which is a continuation of application No. 10/821,638, filed on Apr. 8, 2004, now Pat. No. 7,094,768, which is a continuation-in-part of application No. 10/676,956, filed on Sep. 30, 2003, now Pat. No. 7,425,547.

(60) Provisional application No. 60/443,169, filed on Jan. 29, 2003, provisional application No. 60/415,222, filed on Sep. 30, 2002.

(51) Int. Cl.
A61K 31/70 (2006.01)
C07H 19/14 (2006.01)

(52) U.S. Cl. .................. 514/45; 536/26.23; 536/26.26; 536/26.7; 536/27.2

(58) Field of Classification Search .................. None
See application file for complete search history.

(56) References Cited

U.S. PATENT DOCUMENTS

| | | | |
|---|---|---|---|
| 5,430,027 A | 7/1995 | Knutsen et al. | |
| 5,681,941 A | 10/1997 | Cook et al. | |
| 5,763,167 A * | 6/1998 | Conrad | 435/6 |
| 5,977,332 A * | 11/1999 | Martin | 536/23.1 |
| 6,211,154 B1 | 4/2001 | Scarbourough et al. | |
| 6,475,985 B1 * | 11/2002 | Wagner et al. | 514/7 |
| 6,500,946 B1 | 12/2002 | Takamatsu et al. | |
| 6,586,413 B2 | 7/2003 | Liang et al. | |
| 6,660,721 B2 | 12/2003 | Devos et al. | |
| 6,703,394 B2 | 3/2004 | Engelhardt et al. | |
| 6,777,395 B2 * | 8/2004 | Bhat et al. | 514/43 |
| 7,094,768 B2 * | 8/2006 | Roberts et al. | 514/45 |
| 7,425,547 B2 * | 9/2008 | Roberts et al. | 514/46 |
| 7,432,248 B2 * | 10/2008 | Roberts et al. | 514/43 |
| 2003/0130226 A1 * | 7/2003 | Loakes et al. | 514/46 |
| 2007/0015905 A1 | 1/2007 | LaColla et al. | |
| 2007/0032449 A1 | 2/2007 | LaColla et al. | |

FOREIGN PATENT DOCUMENTS

| | | |
|---|---|---|
| EP | 1117669 | 7/2001 |
| WO | WO 94/18215 | 8/1994 |
| WO | WO 95/07919 | 3/1995 |
| WO | WO 02/057287 | 7/2002 |
| WO | WO 02/057425 A2 | 7/2002 |
| WO | WO 03/061576 | 7/2003 |
| WO | WO03/061576 A3 * | 7/2003 |
| WO | WO 03/072757 A2 | 9/2003 |
| WO | WO 2004/028481 | 4/2004 |
| WO | WO 2004/065398 | 8/2004 |

OTHER PUBLICATIONS

Beigelman et al. "New Syntheses of 2'-C-Methylnucleosides Starting from D-Glucose and D-Ribose" Carbo. Research, 166:219-232 (1987).
Bowler et al., "New Adenosine A3 Ligands Controlling Cytokines," Drug Development Research, 37, 173 (bottom of col. 2) (Mar. 1996).
Jacobson et al., "Recent Developments in Selective Agonists and Antagonists Acting at Purine and Pyrimidine Receptors," Drug Development Research, 39(3-4), 289-300 (1996).
Hinshaw, et al. "Pyrrolopyrimidine nucleosides. IV. Synthesis of certain 4, 5-disubstituted-7-(.beta.-D-ribofuranosy 1)pyrrolo[2,3-d]pyrimidine nucleoside antibiotics" J. of Heterocyclic Chemistry 6(2):215-221 CODEN: JHTCAD; ISSN: 0022-152X, (1969) XP002388343.
Hinshaw, et al. "Pyrrolopyrimidine nucleosides. X. Synthesis of 4,5-disubstituted 7-(.beta.-D-ribofuranosyl)pyrrolo[2,3-d]py rimidines related to toyocamycin and sangivamycin" J. of the Chemical Society, Perkin Transactions: Organic and Bio-Organic Chemistry (1972-1999), (13), 1248-53 CODEN: JCPRB4; ISSN: 0300-922X (1975), XP009068854.
Ding, et al. "Synthesis of 2'-beta-C-methyl toyocamycin and sangivamycin analogues as potential HCV inhibitors" Bioorganic & Medicinal Chemistry Letters, Oxford, GB 15(3):725-727 (Feb. 1, 2005).

* cited by examiner

*Primary Examiner*—Lawrence E Crane
(74) *Attorney, Agent, or Firm*—Robert (Steve) Thomas

(57) ABSTRACT

Disclosed are methods for treating hepatitis C viral infections using deaza-purine compounds of Formula I:

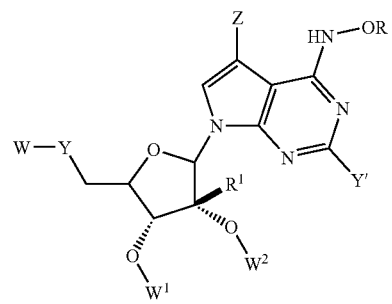

wherein W, $W^1$, $W^2$, Y, $R^1$, Z, Y' and R are as defined herein.

5 Claims, No Drawings

NUCLEOSIDE DERIVATIVES FOR TREATING HEPATITIS C VIRUS INFECTION

CROSS-REFERENCE TO RELATED APPLICATIONS

This application is a continuation of U.S. patent application Ser. No. 11/492,558, filed Jul. 24, 2006, issued as U.S. Pat. No. 7,432,248, which is a continuation of U.S. patent application Ser. No. 10/821,638, filed Apr. 8, 2004, issued as U.S. Pat. No. 7,094,768, which is a continuation-in-part of U.S. patent application Ser. No. 10/676,956, filed on Sep. 30, 2003, issued as U.S. Pat. No. 7,425,547, which claims the benefit under 35 U.S.C. § 119(e) of U.S. Provisional Application Ser. No. 60/443,169, filed Jan. 29, 2003 and U.S. Provisional Application Ser. No. 60/415,222, filed Sep. 30, 2002. Each of these applications are incorporated herein by reference in their entirety.

FIELD OF THE INVENTION

The invention relates to the field of pharmaceutical chemistry, in particular to compounds, compositions and methods for treating viral infections in mammals mediated, at least in part, by a virus in the flaviviridae family of viruses. This invention also relates to compounds, compositions and methods for treating hepatitis C viral infections.

REFERENCES

The following publications are cited in this application as superscript numbers:

1. Chen, et al., Med. Assoc., 95(1):6-12 (1996)
2. Cornberg, et al., "Hepatitis C: therapeutic perspectives." Forum (Genova), 11(2):154-62 (2001)
3. Dymock, et al., Antivir. Chem. Chemother. 11(2):79-96 (2000)
4. Devos, et al., International Patent Application Publication No. WO 02/18404 A2, published 7 Mar. 2002
5. Sommadossi, et al., International Patent Application Publication No. WO 01/90121, published 23 May 2001
6. Carroll, et al., International Patent Application Publication No. WO 02/057425
7. Seela, F.; Steker, H., *Liebigs Ann. Chem., p.* 1576 (1983).
8. Li, N-.S.; Tang, X.-Q.; Piccirilli, J. A., *Organic Letters*, 3(7):1025 (2001).

All of the above publications are herein incorporated by reference in their entirety to the same extent as if each individual publication was specifically and individually indicated to be incorporated by reference in its entirety.

STATE OF THE ART

Hepatitis C virus (HCV) causes a liver damaging infection that can lead to cirrhosis, liver failure or liver cancer, and eventually death. HCV is an enveloped virus containing a positive-sense single-stranded RNA genome of approximately 9.4 kb, and has a virion size of 30-60 nm.[1]

HCV is a major causative agent for post-transfusion and for sporadic non-A, non-B hepatitis. Infection by HCV is insidious in a high proportion of chronically infected (and infectious) carriers who may not experience clinical symptoms for many years.

HCV is difficult to treat and it is estimated that there are 500 million people infected with it worldwide. No effective immunization is currently available, and hepatitis C can only be controlled by other preventive measures such as improvement in hygiene and sanitary conditions and interrupting the route of transmission.

At present, the only acceptable treatment for chronic hepatitis C is interferon (IFN-alpha) and this requires at least six (6) months of treatment and/or ribavirin, which can inhibit viral replication in infected cells and also improve liver function in some people.

IFN-alpha belongs to a family of naturally occurring small proteins with characteristic biological effects such as antiviral, immunoregulatory and antitumoral activities that are produced and secreted by most animal nucleated cells in response to several diseases, in particular, viral infections. IFN-alpha is an important regulator of growth and differentiation affecting cellular communication and immunological control. Treatment of HCV with interferon, however, has limited long term efficacy with a response rate about 25%. In addition, treatment of HCV with interferon has frequently been associated with adverse side effects such as fatigue, fever, chills, headache, myalgias, arthralgias, mild alopecia, psychiatric effects and associated disorders, autoimmune phenomena and associated disorders and thyroid dysfunction.

Ribavirin (1-β-D-ribofuranosyl-1H-1,2,-4-triazole-3-carboxamide), an inhibitor of inosine 5'-monophosphate dehydrogenase (IMPDH), enhances the efficacy of IFN-alpha in the treatment of HCV. Despite the introduction of ribavirin, more than 50% of the patients do not eliminate the virus with the current standard therapy of interferon-alpha (IFN) and ribavirin. By now, standard therapy of chronic hepatitis C has been changed to the combination of PEG-IFN plus ribavirin. However, a number of patients still have significant side effects, primarily related to ribavirin. Ribavirin causes significant hemolysis in 10-20% of patients treated at currently recommended doses, and the drug is both teratogenic and embryotoxic.

Other approaches are being taken to combat the virus. They include, for example, application of antisense oligonucleotides or ribozymes for inhibiting HCV replication. Furthermore, low-molecular weight compounds that directly inhibit HCV proteins and interfere with viral replication are considered as attractive strategies to control HCV infection. NS3/4A serine protease, ribonucleic acid (RNA) helicase, RNA-dependent RNA polymerase are considered as potential targets for new drugs.[2,3]

Devos, et al.[4] describes purine and pyrimidine nucleoside derivatives and their use as inhibitors of HCV RNA replication.

Sommadossi, et al.[5] describes 1', 2' or 3'-modified nucleosides and their use for treating a host infected with HCV.

Given the fact of the worldwide epidemic level of HCV, there is a strong need for new effective drugs for HCV treatment. The present invention provides nucleoside derivatives for treating HCV infections.

SUMMARY OF THE INVENTION

This invention is directed to novel compounds that are useful in the treatment of HCV in mammals. Specifically, in one aspect, the compounds of this invention are represented by Formula I below:

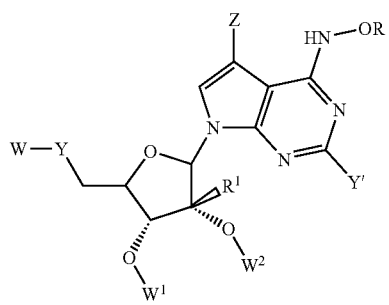

I wherein:

W, $W^1$ and $W^2$ are independently selected from the group consisting of hydrogen and a pharmaceutically acceptable prodrug;

R is selected from the group consisting of hydrogen or $(C_1$-$C_3)$alkyl;

$R^1$ is selected from the group consisting of hydrogen, alkyl, substituted alkyl, alkenyl, substituted alkenyl, alkynyl and substituted alkynyl;

Y is a bond, —$CH_2$— or —O—;

Y' is selected from the group consisting of hydrogen, halo, hydroxyl, thioalkyl, amino and substituted amino;

Z is selected from the group consisting of acyl, cyano, carboxyl, carboxyl ester, —C(O)$NR^{20}R^{21}$, halo, —B(OH)$_2$, —C(=$NR^2$)$R^3$, nitro, alkenyl, substituted alkenyl, acetylenyl and substituted acetylenyl of the formula —C≡C—$R^4$;

where $R^2$ is selected from the group consisting of hydrogen, —OH, —$OR^5$ amino, substituted amino, and $(C_1$-$C_2)$ alkyl, where $R^5$ is selected from the group consisting of alkyl and substituted alkyl;

$R^3$ is selected from the group consisting of hydrogen, alkyl, substituted alkyl, amino and substituted amino;

$R^4$ is selected from the group consisting of hydrogen, phenyl, substituted phenyl, heteroaryl, substituted heteroaryl, —Si($R^8$)$_3$, carboxyl, carboxyl esters, and —C(O)$NR^6R^7$ where $R^6$ and $R^7$ are independently hydrogen, alkyl or $R^6$ and $R^7$ together with the nitrogen atom pendent thereto are joined to form a heterocyclic, substituted heterocyclic, heteroaryl or substituted heteroaryl group;

each $R^8$ is independently $(C_1$-$C_4)$alkyl or phenyl; and $R^{20}$ and $R^{21}$ are independently hydrogen, alkyl, substituted alkyl, aryl, substituted aryl, heteroaryl, substituted heteroaryl, heterocyclic and substituted heterocyclic or $R^{20}$ and $R^{21}$, together with the nitrogen atom pendent thereto form a heterocyclic or substituted heterocyclic group;

or pharmaceutically acceptable salts thereof.

In one preferred embodiment, W is preferably selected from the group consisting of hydrogen, monophosphate, diphosphate, and triphosphate and $W^1$ and $W^2$ are independently hydrogen or acyl. Preferred acyl groups include acetyl and trimethylacetyl, and acyl groups derived from amino acids.

In another aspect, the compounds of this invention are represented by Formula II below:

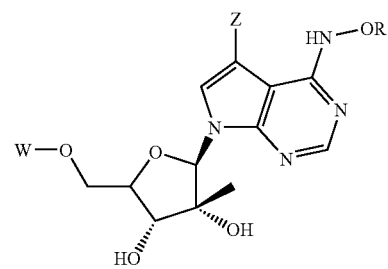

where R, W and Z are as defined above;
or pharmaceutically acceptable salts thereof.

In preferred embodiment, W is preferably selected from the group consisting of hydrogen, monophosphate, diphosphate, and triphosphate.

In the compounds of formula I and II above, Z is preferably selected from the group consisting of acyl, nitro, halo, cyano, —C(=$NR^2$)$R^3$, acetylenyl and substituted acetylenyl of the formula —C≡C—$R^4$ where $R^2$, $R^3$ and $R^4$ are as defined above.

Even more preferably, Z is selected from formyl, nitro, bromo, iodo, and —C≡C—$R^4$ where $R^4$ is selected from H, phenyl, and —Si($CH_3$)$_3$.

In one embodiment, when Z is an alkenyl or substituted alkenyl group, such groups are preferably in the cis orientation if the substituent has a cis/trans relationship.

Compounds included within the scope of this invention include, for example, those set forth below (including pharmaceutically acceptable salts thereof) in Table I:

TABLE I

I

| # | Structure | Name |
|---|-----------|------|
| 1 | 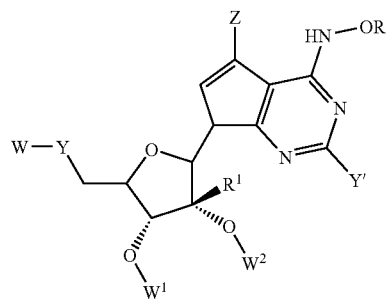 | 1-(6-hydroxylamino-7-ethynyl-7-deazapurin-9-yl)-2-methyl-β-D-ribofuranose |

TABLE I-continued

| # | Structure | Name |
|---|---|---|
| 2 | | 1-(6-hydroxylamino-7-(2-phenylethyn-1-yl)-7-deazapurin-9-yl)-2-methyl-β-D-ribofuranose |
| 3 | | 1-(6-hydroxylamino-7-(2-(pyridin-2-yl)-ethyn-1-yl)-7-deazapurin-9-yl)-2-methyl-β-D-ribofuranose |
| 4 | 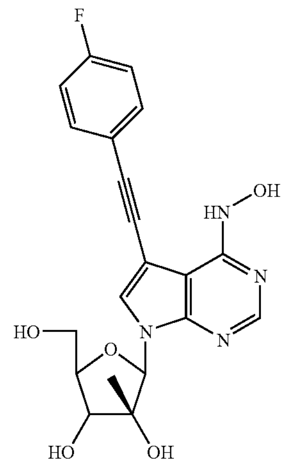 | 1-(6-hydroxylamino-7-(2-(4-fluorophenyl)ethyn-1-yl)-7-deazapurin-9-yl)-2-methyl-β-D-ribofuranose |
| 5 | 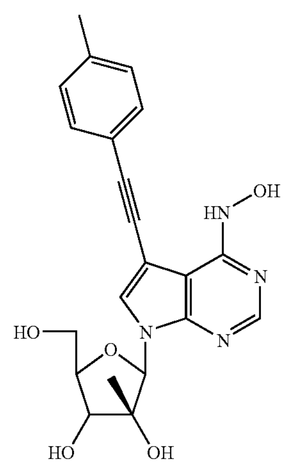 | 1-(6-hydroxylamino-7-(2-(4-methylphenyl)ethyn-1-yl)-7-deazapurin-9-yl)-2-methyl-β-D-ribofuranose |
| 6 | 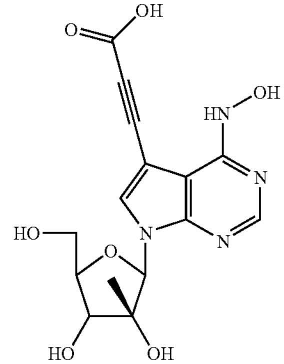 | 1-(6-hydroxylamino-7-(2-carboxylethyn-1-yl)-7-deazapurin-9-yl)-2-methyl-β-D-ribofuranose |

TABLE I-continued

| # | Structure | Name |
|---|---|---|
| 7 | | 1-(6-hydroxylamino-7-(2-ethylcarboxylethyn-1-yl)-7-deazapurin-9-yl)-2-methyl-β-D-ribofuranose |
| 8 | | 1-(6-hydroxylamino-7-(2-carboxamidoethyn-1-yl)-7-deazapurin-9-yl)-2-methyl-β-D-ribofuranose |
| 9 | | 1-(6-hydroxylamino-7-(2-trimethylsilylethyn-1-yl)-7-deazapurin-9-yl)-2-methyl-β-D-ribofuranose |
| 10 | 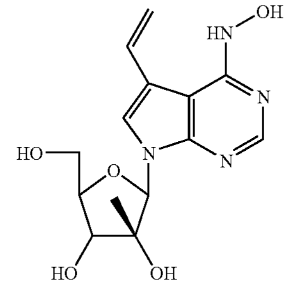 | 1-(6-hydroxylamino-7-ethenyl-7-deazapurin-9-yl)-2-methyl-β-D-ribofuranose |
| 11 | 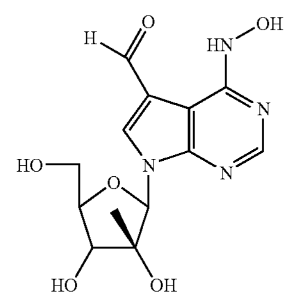 | 1-(6-hydroxylamino-7-formyl-7-deazapurin-9-yl)-2-methyl-β-D-ribofuranose |
| 12 | 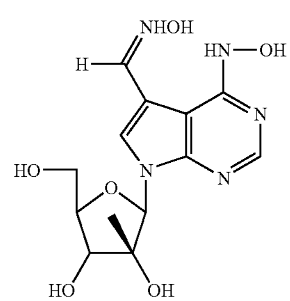 | 1-(6-hydroxylamino-7-(carbaldehyde oxime))-7-deazapurin-9-yl)-2-methyl-β-D-ribofuranose; |
| 13 | 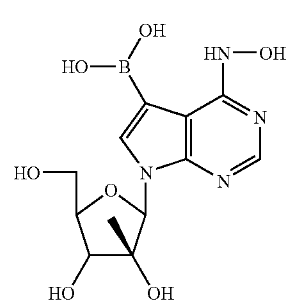 | 1-(6-hydroxylamino-7-(boronic acid)-7-deazapurin-9-yl)-2-methyl-β-D-ribofuranose |

TABLE I-continued

| # | Structure | Name |
|---|---|---|
| 14 | 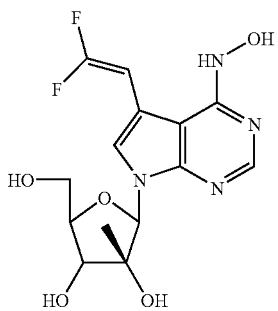 | 1-(6-hydroxylamino-7-(2,2-difluorovinyl)-7-deazapurin-9-yl)-2-methyl-β-D-ribofuranose |
| 15 | 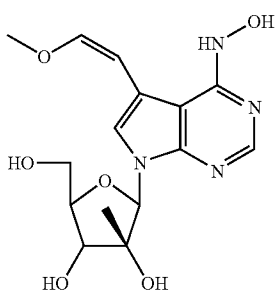 | 1-(6-hydroxylamino-7-(2-cis-methoxyvinyl)-7-deazapurin-9-yl)-2-methy-β-D-ribofuranose |
| 16 | 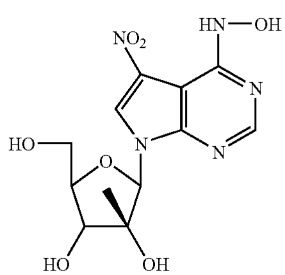 | 1-(6-hydroxylamino-7-nitro-7-deazapurin-9-yl)-2-methyl-β-D-ribofuranose |
| 17 | 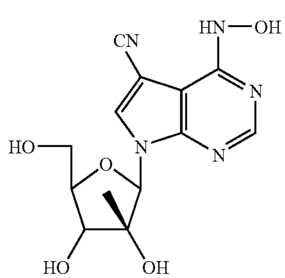 | 1-(6-hydroxylamino-7-cyano-7-deazapurin-9-yl)-2-methyl-β-D-ribofuranose |
| 18 | | 1-(6-methoxyamino-7-ethynyl-7-deazapurin-9-yl)-2-methyl-β-D-ribofuranose |
| 19 | | 1-(6-methoxyamino-7-nitro-7-deazapurin-9-yl)-2-methyl-β-D-ribofuranose |
| 20 | | 1-(6-methoxyamino-7-formyl-7-deazapurin-9-yl)-2-methyl-β-D-ribofuranose |

This invention is also directed to pharmaceutical compositions comprising a pharmaceutically acceptable diluent and a therapeutically effective amount of a compound of this invention or mixtures of one or more of such compounds.

This invention is still further directed to methods for treating a viral infection mediated at least in part by a virus in the flaviviridae family of viruses, such as HCV, in mammals which methods comprise administering to a mammal, that has been diagnosed with said viral infection or is at risk of developing said viral infection, a pharmaceutical composition comprising a pharmaceutically acceptable diluent and a therapeutically effective amount of compounds of this invention or mixtures of one or more of such compounds.

DETAILED DESCRIPTION OF THE INVENTION

The invention is directed to compounds, compositions and methods for treating flaviviridae viruses, such as hepatitis C virus infections. However, prior to describing this invention in detail, the following terms will first be defined:

Definitions

Unless otherwise limited by the term as used elsewhere herein, the following terms have the following meanings:

"Alkyl" refers to alkyl groups having from 1 to 5 carbon atoms and more preferably 1 to 3 carbon atoms. The alkyl group may contain linear or branched carbon chains. This term is exemplified by groups such as methyl, ethyl, n-propyl, iso-propyl, n-butyl, t-butyl, n-pentyl and the like. The term $C_1$-$C_2$ alkyl refers to an alkyl group having one or two carbon atoms.

"Substituted alkyl" refers to an alkyl group having from 1 to 3, and preferably 1 to 2, substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)— and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NR$^{10}$R$^{10}$ where each R$^{10}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R$^{10}$ is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 6 carbon atoms and more preferably 2 to 4 carbon atoms and having at least 1 and preferably from 1-2 sites of alkenyl unsaturation. Such groups are exemplified by vinyl, allyl, but-3-en-1-yl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic with the proviso that any hydroxyl substitution is not attached to a vinyl (unsaturated) carbon atom.

"Alkynyl" refers to alkynyl group preferably having from 2 to 6 carbon atoms and more preferably 2 to 3 carbon atoms and having at least 1 and preferably from 1-2 sites of alkynyl unsaturation. A preferred alkynyl is $C_2$ alkynyl which is sometimes referred to herein as acetylenyl: —C≡CH.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. A preferred substituted alkynyl is substituted acetylenyl which can be represented by the formula: —C≡CR$^4$ where R$^4$ is as defined herein.

"Amino" refers to the group —NH$_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic or substituted heterocylic group provided that R' and R" are both not hydrogen. When R' is hydrogen and R" is alkyl, the substituted amino group is sometimes referred to herein as alkylamino. When R' and R" are alkyl, the substituted amino group is sometimes referred to herein as dialkylamino.

"Aminoacyl" refers to the groups —NR$^{11}$C(O)alkyl, —NR$^{11}$C(O)substituted alkyl, —NR$^{11}$C(O)cycloalkyl, —NR$^{11}$C(O)substituted cycloalkyl, —NR$^{11}$C(O)alkenyl, —NR$^{11}$C(O)substituted alkenyl, —NR$^{11}$C(O)alkynyl, —NR$^{11}$C(O)substituted alkynyl, —NR$^{11}$C(O)aryl, —NR$^{11}$C(O)substituted aryl, —NR$^{11}$C(O)heteroaryl, —NR$^{11}$C(O)substituted heteroaryl, —NR$^{11}$C(O)heterocyclic, and —NR$^{11}$C(O)substituted heterocyclic where R$^{11}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryls include phenyl and naphthyl.

"Substituted aryl" refers to aryl groups including phenyl groups (sometimes referred to herein as "substituted phenyl") which are substituted with from 1 to 3 substituents, and preferably 1 to 2 substituents, selected from the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy.

"Aryloxy" refers to the group aryl-O— that includes, by way of example, phenoxy, naphthoxy, and the like.

"Substituted aryloxy" refers to substituted aryl-O— groups.

"Carboxyl" refers to —COOH or salts thereof.

"Carboxyl esters" refers to the groups —C(O)O-alkyl, —C(O)O-substituted alkyl, —C(O)Oaryl, and —C(O)O-substituted aryl wherein alkyl, substituted alkyl, aryl and substituted aryl are as defined herein.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Substituted cycloalkyl" refers to an cycloalkyl group, having from 1 to 5 substituents selected from the group consisting of oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Halo" or "halogen" refers to fluoro, chloro, bromo and iodo and preferably is fluoro or chloro.

"Heteroaryl" refers to an aromatic group of from 1 to 10 carbon atoms and 1 to 4 heteroatoms selected from the group consisting of oxygen, nitrogen, sulfur, —S(O)—, and —S(O)$_2$— within the ring. Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Preferred heteroaryls include pyridyl, pyrrolyl, indolyl, thiophenyl, and furyl.

"Substituted heteroaryl" refers to heteroaryl groups that are substituted with from 1 to 3 substituents selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" or "heterocycloalkyl" refers to a saturated or unsaturated, but not heteroaromatic, group having a single ring or multiple condensed rings, from 1 to 10 carbon atoms and from 1 to 4 hetero atoms selected from the group consisting of nitrogen, oxygen, sulfur, —S(O)— and —S(O)$_2$— within the ring wherein, in fused ring systems, one or more of the rings can be cycloalkyl, aryl or heteroaryl provided that the point of attachment is through the heterocyclic ring.

"Substituted heterocyclic" or "substituted heterocycloalkyl" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Phosphate" refers to the groups —P(O)(OH)$_2$ (monophosphate), —P(O)(OH)OP(O)(OH)$_2$ (diphosphate) and —P(O)(OH)OP(O)(OH)OP(O)(OH)$_2$ (triphosphate) or salts thereof including partial salts thereof.

"Phosphonate" refers to the groups —P(O)(R$^{12}$)(OH) or —P(O)(R$^{12}$)(OR$^{13}$) or salts thereof including partial salts thereof, wherein each R$^{12}$ is independently selected from hydrogen, alkyl, substituted alkyl, carboxylic acid, and carboxyl ester and R$^{13}$ is alkyl or substituted alkyl.

"Sulfonate ester" refers to the groups —SO$_2$OR$^{14}$ where R$^{14}$ is selected from the group consisting of alkyl, substituted alkyl, alkenyl, substituted alkenyl, aryl, substituted aryl, heteroaryl, substituted heteroaryl, heterocyclic and substituted heterocyclic.

"Thiol" refers to the group —SH.

"Thioalkyl" or "alkylthioether" or "thioalkoxy" refers to the group —S-alkyl.

"Substituted thioalkyl" or "substituted alkylthioether" or "substituted thioalkoxy" refers to the group —S-substituted alkyl.

"Thiocycloalkyl" refers to the groups —S-cycloalkyl and "substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

The term "amino acid" refers to α-amino acids of the formula H$_2$NCH(R$^{15}$)COOH where R$^{15}$ is hydrogen, alkyl, substituted alkyl, aryl or substituted aryl. Preferably, the α-amino acid is one of the twenty naturally occurring L amino acids.

The term "carbohydrate" refers to oligosaccharides comprising from 2 to 20 saccharide units. The particular saccharide units employed are not critical and include, by way of example, all natural and synthetic derivatives of glucose, galactose, N-acetylglucosamine, N-acetylgalactosamine, fucose, sialic acid, and the like. In addition to being in their pyranose form, all saccharide units described herein are in their D form except for fucose which is in its L form.

The term "lipid" is an art recognized term defined, for example, by Lehninger, *Biochemistry,* 1970, at pages 189 et seq. which is incorporated herein by reference in its entirety.

The term "peptide" refers to polymers of α-amino acids comprising from about 2 to about 20 amino acid units, preferably from about 2 to about 10, more preferably from about 2 to about 5.

The term "stabilized phosphate prodrug" refers to mono-, di- and tri-phosphate groups having one or more of the hydroxyl groups pendent thereto converted to an alkoxy, a substituted alkoxy group, an aryloxy or a substituted aryloxy group.

The term "pharmaceutically acceptable prodrugs" refers to art recognized modifications to one or more functional groups which functional groups are metabolized in vivo to provide a compound of this invention or an active metabolite thereof. Such functional groups are well known in the art including acyl groups for hydroxyl and/or amino substitution, esters of mono-, di- and tri-phosphates wherein one or more of the pendent hydroxyl groups have been converted to an alkoxy, a substituted alkoxy, an aryloxy or a substituted aryloxy group, and the like.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

General Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis,* Third Edition, Wiley, New York, 1999, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Still further, some of the compounds defined herein include vinyl groups which can exist in cis, trans or a mixture of cis and trans forms. All combinations of these forms are within the scope of this invention.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, $4^{th}$ Edition), and Larock's Comprehensive Organic Transformations (VCH Publishers Inc., 1989). Specifically, the compounds of this invention may be prepared by various methods known in the art of organic chemistry in general and nucleoside and nucleotide analogue synthesis in particular. General reviews of the preparation of nucleoside and nucleotide analogues include 1) Michelson A. M. "*The Chemistry of Nucleosides and Nucleotides,*" Academic Press, New York, 1963; 2) Goodman L. "*Basic Principles in Nucleic Acid Chemistry,*" Academic Press, New York, 1974, vol. 1, Ch. 2; and 3) "*Synthetic Procedures in Nucleic Acid Chemistry,*" Eds. Zorbach W. & Tipson R., Wiley, New York, 1973, vol. 1 & 2.

The synthesis of the compounds of this invention generally follows either a convergent or linear synthetic pathway as described below.

The strategies available for synthesis of compounds of this invention include for example:

General Synthesis of 2'-C-Branched Nucleosides
2'-C-Branched ribonucleosides of Formula I:

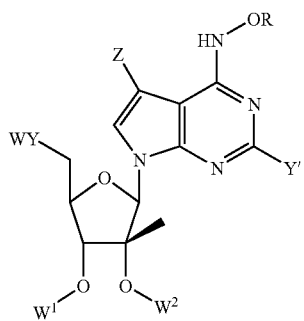

I where R, W, $W^1$, $W^2$, Y, Y' and Z are as defined above, can be prepared by one of the following general methods.

Convergent Approach: Glycosylation of Nucleobase with Appropriately Modified Sugar The key starting material of this process is an appropriately substituted sugar with 2'-OH and 2'-H with the appropriate leaving group, for example, an acyl group or a chloro, bromo, fluoro or iodo group. The sugar can be purchased or can be prepared by any known means including standard epimerization, substitution, oxidation and/or reduction techniques. For example, commercially available 1,3,5-tri-O-benzoyl-α-D-ribofuranose (Pfanstiel Laboratories, Inc.) can be used. The substituted sugar can then be oxidized with the appropriate oxidizing agent in a compatible solvent at a suitable temperature to yield the 2'-modified sugar. Possible oxidizing agents are, for example, Dess-Martin periodine reagent, $Ac_2O$+DCC in DMSO, Swern oxidation (DMSO, oxalyl chloride, triethylamine), Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$, ruthenium tetraoxide, phase transfer catalysts such as chromic acid or permanganate supported on a polymer, $Cl_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Coupling of an organometallic carbon nucleophile, such as a Grignard reagent, an organolithium, lithium dialkylcopper or $R^1$—$SiMe_3$ in TBAF with the ketone with the appropriate non-protic solvent at a suitable temperature, yields the 2'-alkylated sugar. For example, $R^1MgBr/TiCl_4$ or $R^1MgBr/CeCl_3$ can be used as described in Wolfe et al., 1997. *J. Org. Chem.* 62: 1754-1759 (where $R^1$ is as defined herein). The alkylated sugar can be optionally protected with a suitable protecting group, preferably with an acyl, substituted alkyl or silyl group, by methods well known to those skilled in the art, as taught by Greene et al. *Protective Groups in Organic Synthesis*, John Wiley and Sons, Second Edition, 1991.

The optionally protected sugar can then be coupled to the purine base by methods well known to those skilled in the art, as taught by Townsend *Chemistry of Nucleosides and Nucleotides*, Plenum Press, 1994. For example, an acylated sugar can be coupled to a silylated base with a Lewis acid, such as tin tetrachloride, titanium tetrachloride or trimethylsilyltriflate in the appropriate solvent at a suitable temperature. Alternatively, a halo-sugar can be coupled to a silylated base with the presence of trimethylsilyltriflate.

In addition to the above, the 2'-C-substituted sugars used in the synthetic methods described herein are well known in the art and are described, for example, by Sommadossi, et al.[5] and by Carrol, et al.[6] both of which are incorporated herein by reference in their entirety.

Scheme 1 below describes the alternative synthesis of a protected sugar that is useful for coupling to the bases described herein.

Scheme 1: Alternative Sugar Synthesis and Coupling

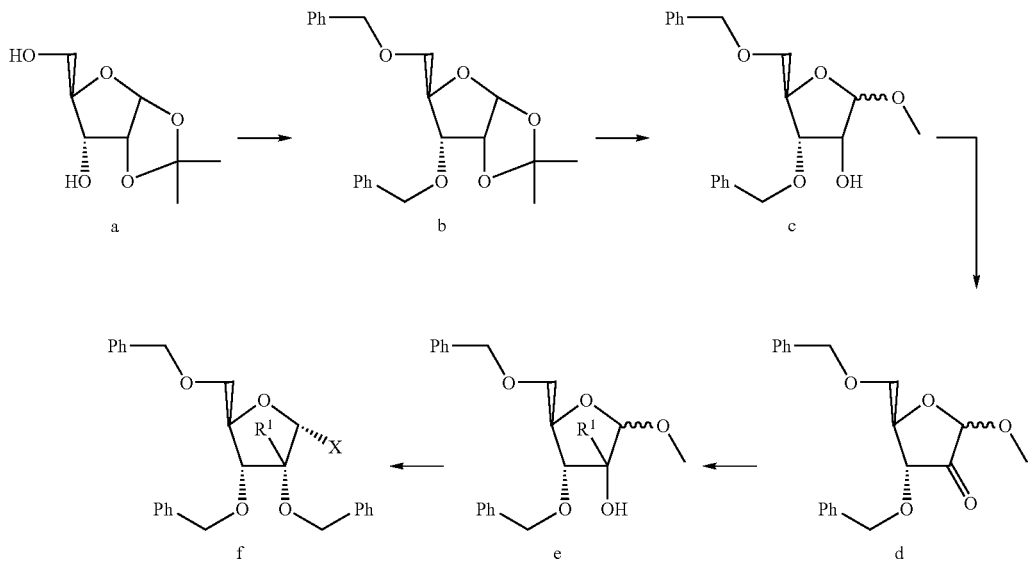

Scheme 1

Formation of sugar a in Scheme 1, above, is accomplished as described by Mandal, S. B., et al., *Synth. Commun.*, 1993, 9, page 1239, starting from commercial D-ribose. Protection of the hydroxyl groups to form sugar b is described in Witty, D. R., et al., *Tet. Lett.*, 1990, 31, page 4787. Sugar c and d are prepared using the method of Ning, J. et al., *Carbohydr. Res.*, 2001, 330, page 165, and methods described herein. $R^1$, in Scheme 1 can be hydrogen, alkyl, substituted alkyl, alkenyl, substituted alkenyl, alkynyl, and substituted alkynyl. Particularly preferred $R^1$ groups are methyl, trifluoromethyl, alkenyl coupling reaction is prepared using the same protection method as used in to make sugar b above. The halogenation is described in Seela.[7]

Subsequently, any of the described nucleosides can be deprotected by methods well known to those skilled in the art, as taught by Greene et al. *Protective Groups in Organic Synthesis*, Jon Wiley and Sons, Second Edition, 1991.

An alternative approach to making protected sugars useful for coupling to heterocyclic bases is detailed in Scheme 2 below. The details for this synthesis can be found in Example 1.

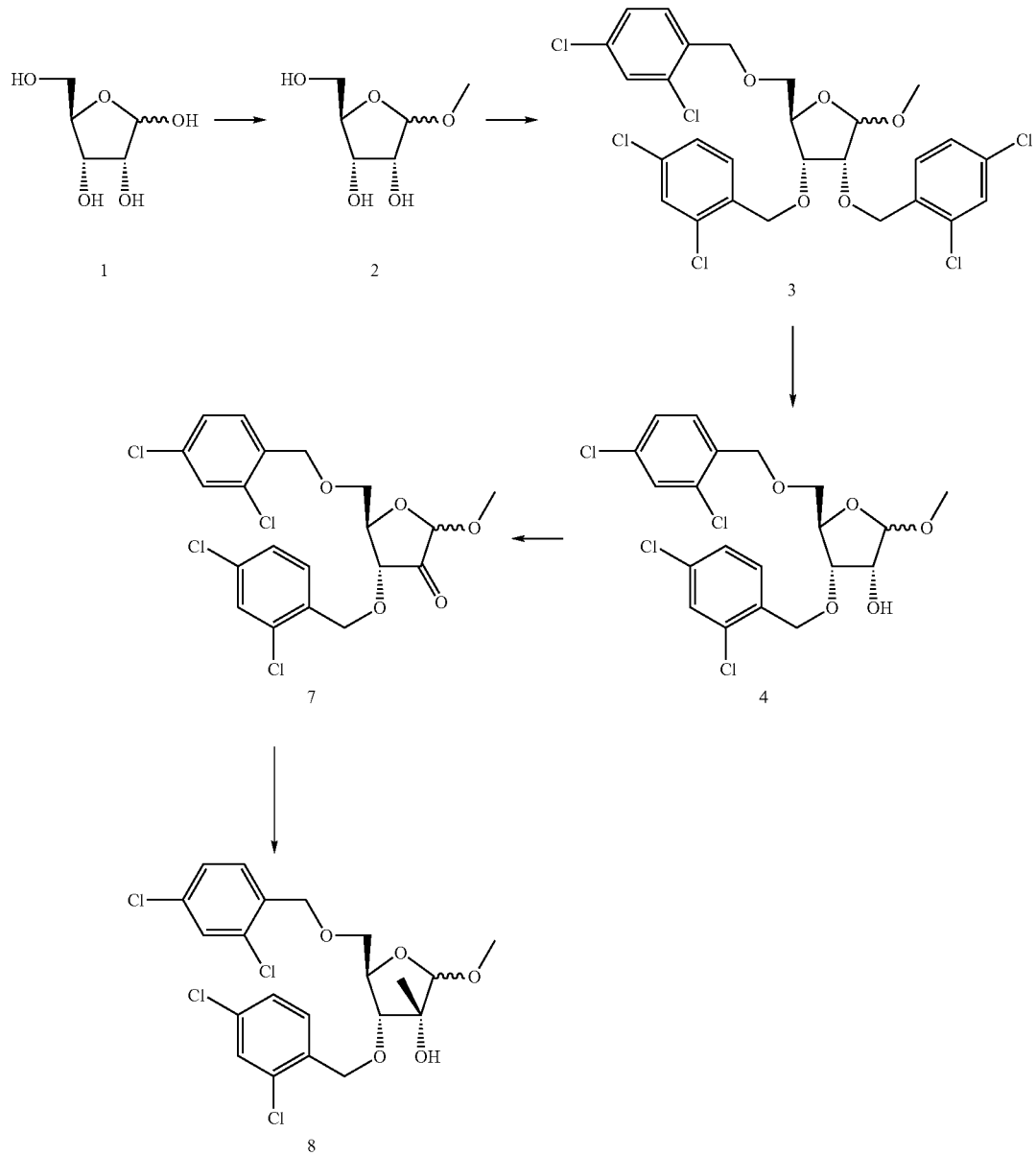

Scheme 2 and alkynyl. Sugar e is prepared by using a modification of the Grignard reaction within $R^1MgBr$ or other appropriate organometallic as described herein (with no titanium/cerium needed). Finally the halogenated sugar used in the subsequent Linear Approach: Modification of a Pre-Formed Nucleoside The key starting material for this process is an appropriately substituted nucleoside with a 2'-OH and 2'-H. The nucleoside can be purchased or can be prepared by any known means including standard coupling techniques. The nucleoside can be optionally protected with suitable protecting groups, preferably with acyl, substituted alkyl or silyl groups, by methods well known to those skilled in the art, as taught by Greene et al. *Protective Groups in Organic Synthesis*, John Wiley and Sons, Second Edition, 1991.

The appropriately protected nucleoside can then be oxidized with the appropriate oxidizing agent in a compatible solvent at a suitable temperature to yield the 2'-modified sugar. Possible oxidizing agents are, for example, Dess-Martin periodine reagent, $Ac_2O+DCC$ in DMSO, Swern oxidation (DMSO, oxalyl chloride, triethylamine), Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$ ruthenium tetroxide, phase transfer catalysts such as chromic acid or permanganate supported on a polymer, $Cl_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide. Coupling of an organometallic carbon nucleophile, such as a Grignard reagent, an organolithium, lithium dialkylcopper or $R^1$—$SiMe_3$ in TBAF with the ketone with the appropriate non-protic solvent at a suitable temperature, yields the appropriate substituted nucleoside.

Subsequently, the nucleoside can be deprotected by methods well known to those skilled in the art, as taught by Greene et al. *Protective Groups in Organic Synthesis*, John Wiley and Sons, Second Edition, 1991.

In one embodiment of the invention, the L-enantiomers are preferred. However, D-enantiomers are also useful herein. The L-enantiomers can be corresponding to the compounds of the invention can be prepared following the same foregoing general methods, beginning with the corresponding L-sugar or nucleoside L-enantiomer as starting material. In a particular embodiment, the 2'-C-branched ribonucleoside is desired. In another embodiment, the 3'-C-branched ribonucleoside is desired.

Scheme 3 below provides a method for preparing 7-nitro-7-deazapurines of the present invention. The preparation of compound 115 from compound 102 (prepared as in Scheme 2 above) and compound 101 has been described elsewhere, (see Carroll, et al., International Patent Application Publication No. WO 02/057425).

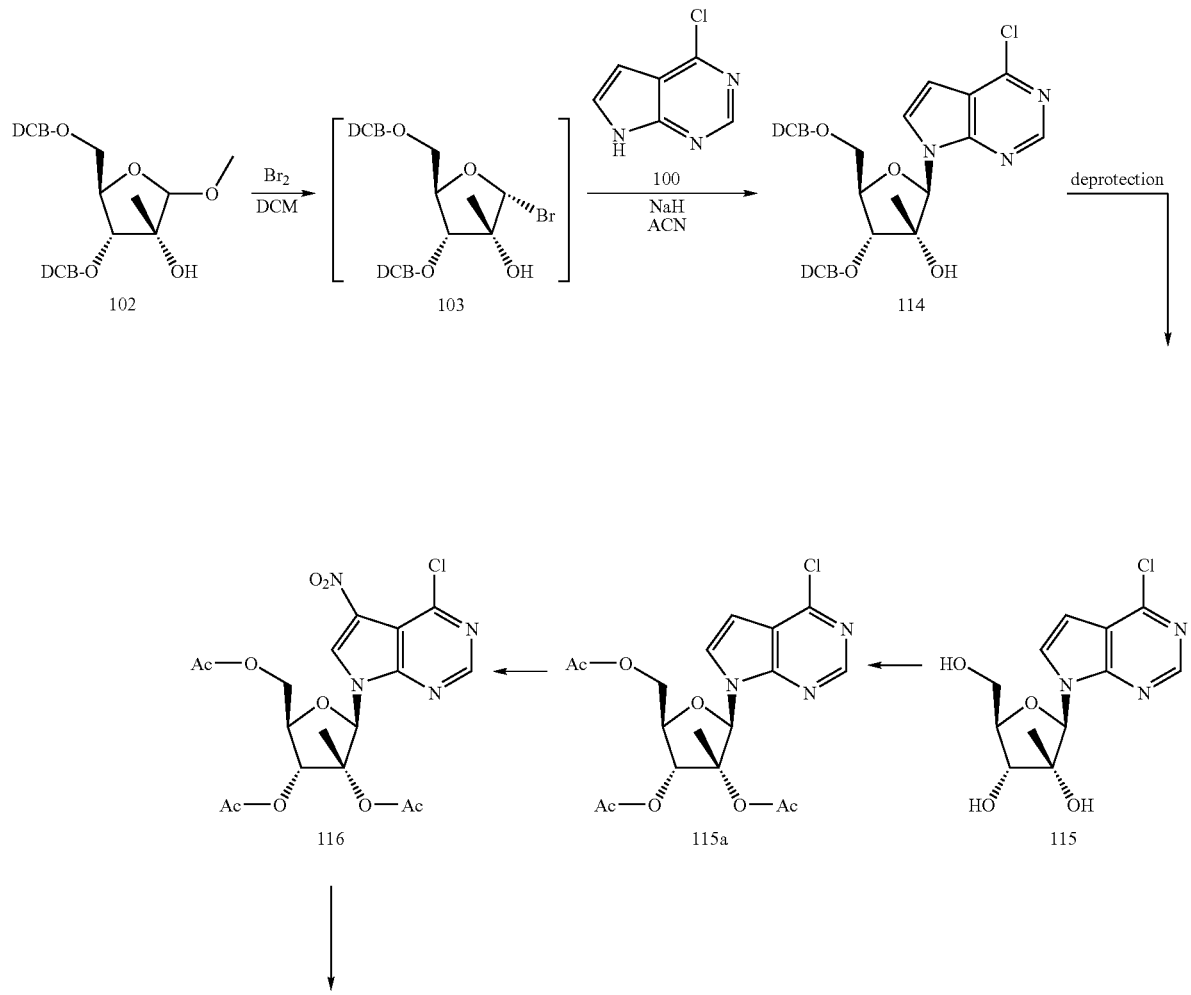

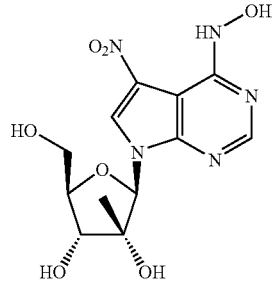

16

The hydroxyl groups of the 6-chloro-deazapurine derivative, compound 115, are protected with acetyl groups by reaction with acetyl chloride and acetic acid to form compound 115a. Compound 115a is converted to the 7-nitor derivative reaction in a 5% (v/v) of an acid solution (1:1 mixture of nitric and sulfuric acid solution) in DCM. The reaction is run at about 0° C. to about room temperature for about 20 minutes, or until the reaction is complete. Hydroxylamine compounds of this invention are prepared by reaction of compound 116 with NH$_2$OH. Methoxyamine derivatives can be prepared in a similar manner using NH$_2$OCH$_3$ in place of the NH$_2$OH.

Scheme 4, below provides a method for preparing 7-halo-7-deazapurine derivatives of the present invention. For example, reaction of commercially available compound 100 with NBS in acetonitrile, using standard conditions provides compound 101. Compound 104 is prepared by coupling compound 101 with compound 103 (which is prepared as described in Scheme 3 above). This coupling reaction is run in the presence of sodium hydride in an inert solvent such as acetonitrile. Deprotection of compound 104 is accomplished by reaction with BCl$_3$ in DCM at about −78° C. to about −20° C. for about 12 hours, providing compound 105. Finally reaction of compound 105 with trimethylsilyl-O-hydroxylamine in a solvent such as ethanol provides the 7-halo-7-deazapurine derivatives. This reaction is run at about 85° C. for about 2 hours. These compounds are useful for the treatment of viral infections, such as HCV. They are also useful as intermediates for preparing other compounds of the present invention.

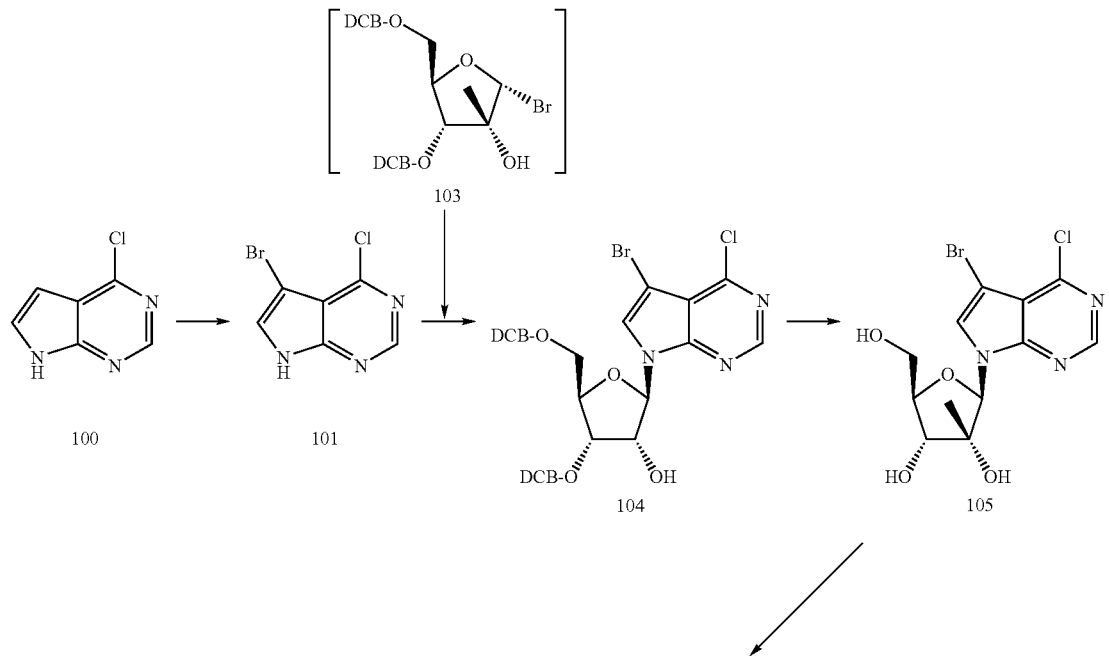

Scheme 4

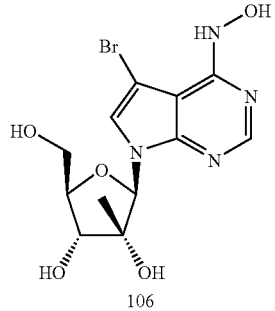

106

The 7-formyl-7-deazapurines of the present invention can be prepared as shown in Scheme 5 below. Compound 104 (prepared as discussed above) is reacted with carbon monoxide in the presence of a catalytic amounts of tributyltin hydride and palladium tetraphenylphosphine in an inert solvent such as THF. This reaction is run for about 24 hours at about 50° C. to provide compound 107. Deprotection of compound 107 as described above provides for compound 109.

Reaction of compound 109 with trimethylsilyl-O-hydroxylamine, as described above, provides for 6-hydroxylamine-7-formyl-7-deazapurines of the present invention.

Alternatively, reaction of compound 109 with $NH_2OCH_3$ in ethanol at about 85° C. for about 2 hours provides compound 20, 6-methoxyamino-7-formyl-7-deazapurine derivatives of the present invention.

Further, the formyl group of compound 109 can be used as an intermediate in the synthesis of alkenyl and substituted alkenyl compounds using conventional Wittig-Horner reaction conditions.

Still further, the formyl group can be oxidized to provide for the corresponding carboxyl group which, optionally, can be esterified by conventional methods to provide for a carboxyl ester or can be amidated by conventional methods to provide for a carboxylamide, e.g., —C(O)NR$^{20}$R$^{21}$ where R$^{20}$ and R$^{21}$ are as defined above.

Scheme 5

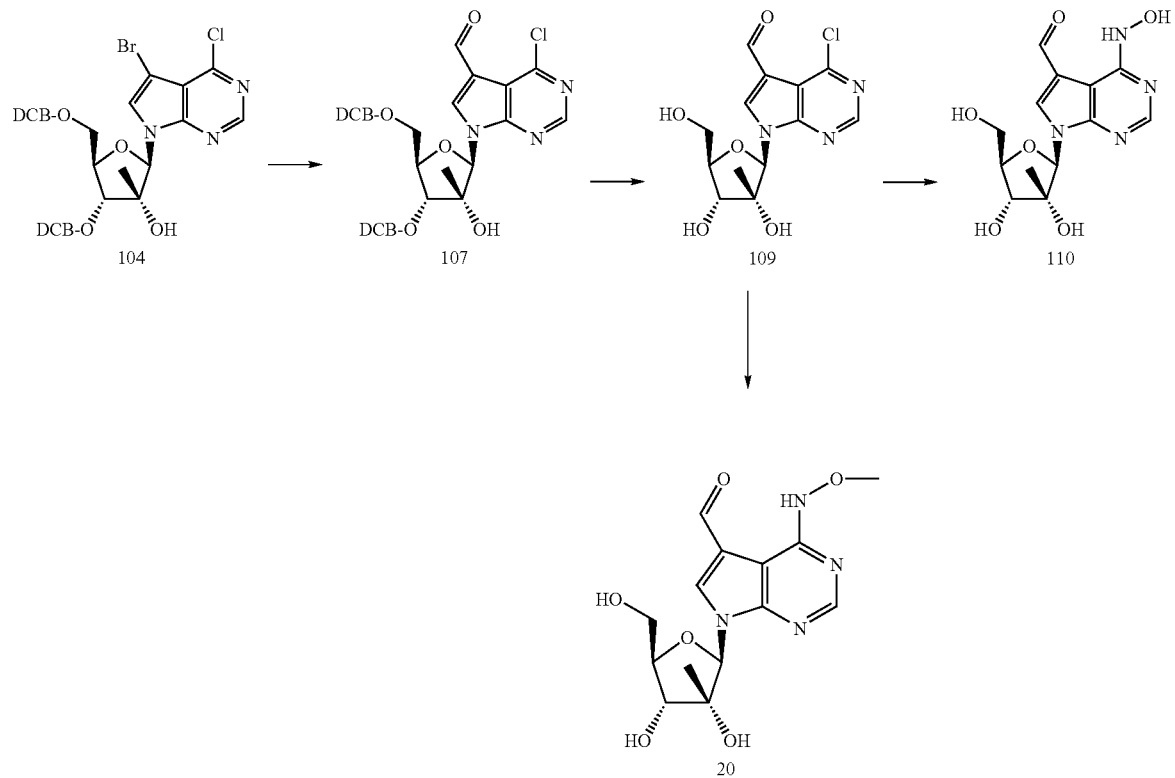

Preparation of the 7-cyano-7-deazapurine derivatives of the present invention are describe in Scheme 6 below. Compound 104 can be treated with tributyltin cyanide and palladium tetraphenylphosphine in an inert solvent such as THF. This reaction is run for about 15 hours at about 50° C. to provide for compound 111, which can be converted to the hydroxylamine or the methoxyamine as described above.

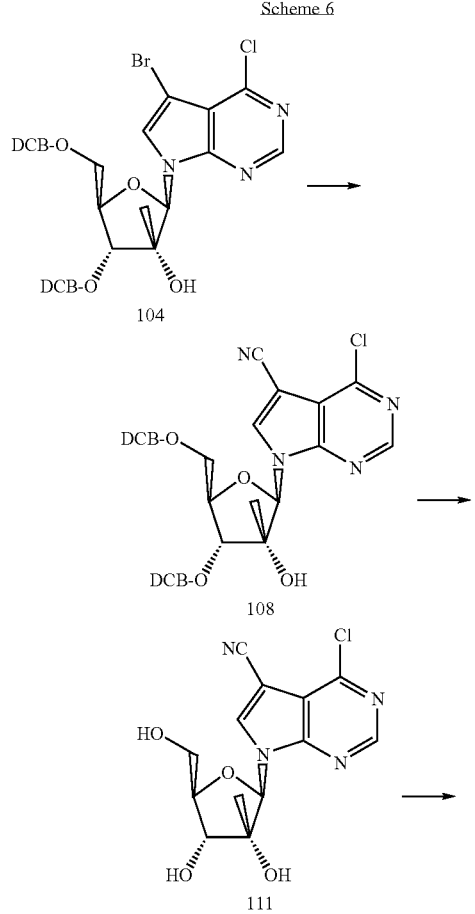

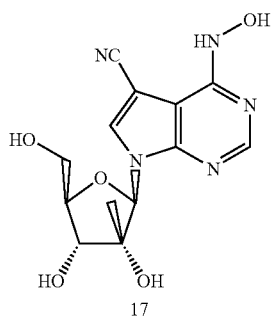

Acetylenic compounds of the present invention can be prepared by the method shown in Scheme 7 below. The details for each reaction step needed to prepare compounds where X is —NHOH can be found in Example 2 below. Specifically, reaction of compound 100 with NIS in a manner similar to that used with NBS in Scheme 4 provides for 7-iodo substituent in compound 118. Coupling of this compound with trimethylsilylacetylene to provide for compound 119 which itself is coupled to sugar 102 under conventional conditions to provide for compound 120. Conventional removal of protecting groups on the sugar provides for compound 121 which is then converted to the hydroxylamine or the alkoxylamine and desilylated to provided for compound 122. As before, conversion to the hydroxylamine employs trimethylsilyl-O-hydroxylamine and conversion to the alkoxyamine employs trialkylsilyl-O-methoxyamine in place of trimethylsilyl-O-hydroxylamine.

It is understood, of course, that the 7-iodo substituent is itself a compound of this invention as well as an intermediate in the synthesis of further compounds. Likewise, the 7-acetylenyl substitute can be derivatized by, e.g., hydrogenation, to provide for the corresponding vinyl compound (not shown).

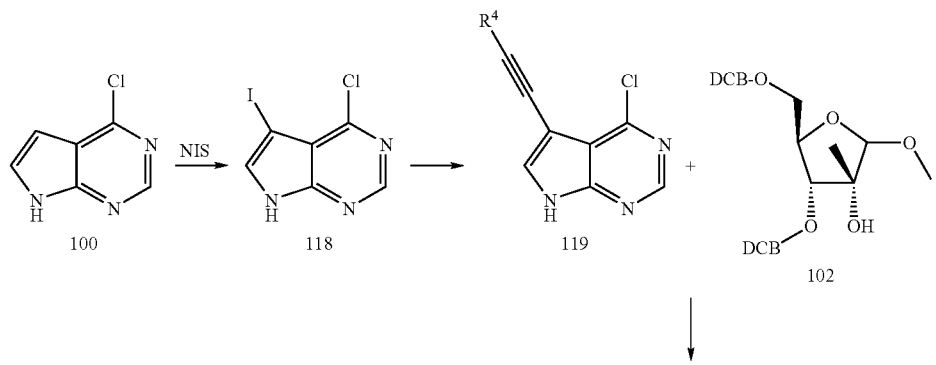

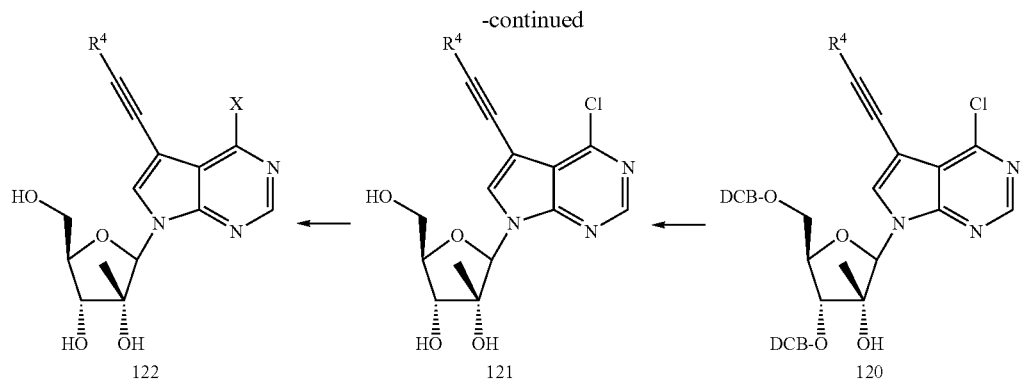

Boronic substituents at the 7-position are prepared according to Scheme 8 below. This methods used to prepare compound 125 are similar to those discussed for the preparation of compound 106 in Scheme 4 above. As stated above, it is understood that the 7-iodo substituent is itself a compound of this invention as well as an intermediate in the synthesis of further compounds.

Conversion of compound 125 to the boronic acid derivative can be accomplished using methods known in the art. For example by reaction with an excess of KOAc (about 3 eq.) in the presence of about 3 mole % $(Ph_3)_2PdCl_2$ and about 1.2 eq. bis(neopenty glycolato)diiboron in an inert solvent such as DMSO (0.15M). This reaction is run at about 65° C. until complete.

Scheme 8

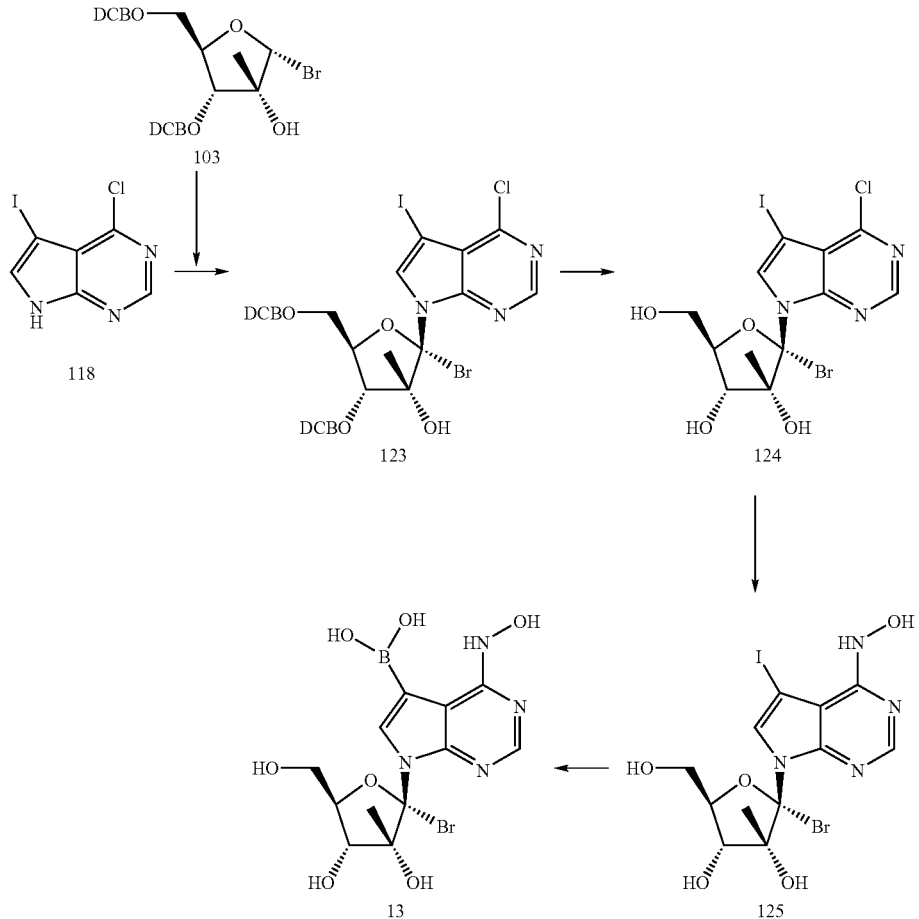

Utility, Testing and Administration

Utility

The present invention provides novel compounds possessing antiviral activity, including hepatitis C virus. The compounds of this invention inhibit HCV replication by inhibiting the enzymes involved in replication, including RNA dependent RNA polymerase. They may also inhibit other enzymes utilized in the activity or proliferation of HCV.

The compounds of the present invention can also be used as prodrug nucleosides. As such they are taken up into the cells and can be intracellularly phosphorylated by kinases to the triphosphate and are then inhibitors of the polymerase (NS5b) and/or act as chain-terminators.

Compounds of this invention maybe used alone or in combination with other compounds to treat viruses.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day.

Therapeutically effective amounts of compounds of this invention may range from approximately 0.05 to 50 mg per kilogram body weight of the recipient per day; preferably about 0.01-25 mg/kg/day, more preferably from about 0.5 to 10 mg/kg/day. Thus, for administration to a 70 kg person, the dosage range would most preferably be about 35-70 mg per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of this invention is inhalation. This is an effective method for delivering a therapeutic agent directly to the respiratory tract, in particular for the treatment of diseases such as asthma and similar or related respiratory tract disorders (see U.S. Pat. No. 5,607,915).

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of this invention or a mixture thereof in combination with at least one pharmaceutically acceptable excipient. Acceptable excipients are non-toxic, aid administration, and do not adversely affect the therapeutic benefit of the compound of this invention. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of a compound of this invention based on the total formulation, with the balance being one or more suitable pharmaceutical excipients. Preferably, the compound is present at a level of about 1-80 wt %. Representative pharmaceutical formulations containing a compound of this invention are described below.

Dosages and Ranges of Compounds

The amount of the composition administered for therapeutic will depend on a number of factors, including but not limited to the desired final concentration of the compound, the pharmacokinetic and pharmacodynamic properties of the compound, the size of the patient, physiological profile of the patient, and the like. The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

Determination of dosages is well within the empiric knowledge of persons skilled in the art; nonetheless, it can be appreciated that estimates of final dosages can be made by approximating the concentration of compound necessary to achieve a desired proteasomic inhibitory, anti-proliferative, anti-cancer or anti-inflammatory activity, such as the activities described above. Further refinement of this dose estimate can be made on the basis of activity in one or more preclinical models, such as the animal models exemplified in Example 16 herein. Extrapolation to a specified mammalian dosage range, or more particularly a human dosage range is well within the skill of the practitioner.

Typically, the amount of a single administration of a composition of the present invention can be about 0.1 to about 1000 mg per kg body weight, or about 0.5 to about 10,000 mg per day. Any of these doses can be further subdivided into separate administrations, and multiple dosages can be given to any individual patient.

In some embodiments, compositions are administered in one dosing of a single formulation and in other embodiments, compositions are administered in multiple dosing of a single formulation within a specified time period. In some embodiments, the time period is between about 3 hours to about 6 hours. In other embodiments, the time period is between about 6 hours and 12 hours. In additional embodiments, the time period is between about 12 hours and 24 hours. In yet further embodiments, the time period is between about 24 hours and 48 hours. The administration of separate formulations can be simultaneous or staged throughout a specified time period, such that all ingredients are administered within the specified time period.

EXAMPLES

The examples below as well as throughout the application, the following abbreviations have the following meanings. If not defined, the terms have their generally accepted meanings.

| | |
|---|---|
| AcOH or HOAc = | acetic acid |
| Ac$_2$O = | acetic anhydride |
| atm = | atmosphere |
| CAN = | ceric ammonium nitrate |
| cm = | centimeter |
| d = | doublet |
| dd = | doublet of doublets |
| dec = | decomposes |
| DCB = | 2,4,-dichlorobenzyl |
| DCC = | N,N-dicyclohexyl carbodiamide |
| DCM = | dichloromethane |
| DMAP = | dimethylaminopyridine |
| DMEM = | Delbecco's minimum eagles medium |
| DMF = | N,N-dimethylformamide |
| DMSO = | dimethylsulfoxide |
| DTT = | dithiothreitol |
| EDTA = | ethylene diamine tetraacetic acid |
| eq. or equiv. = | equivalents |
| g = | gram |
| h = | hour |
| HCV = | hepatitis C virus |
| HPLC = | high performance liquid chromatography |
| IPTG = | isopropyl-b-D-thiogalactopyranoside |
| IU = | international units |
| kb = | kilobase |
| kg = | kilogram |
| L = | liter |
| m = | multiplet |
| M = | molar |

-continued

| | |
|---|---|
| mg = | milligram |
| mL or ml = | milliliter |
| mM = | millimolar |
| mmol = | millimol |
| MS = | mass spectrum |
| ng = | nanograms |
| nm = | nanometers |
| nM = | nanomolar |
| NBS = | N-bromosuccinimide |
| NIS = | N-iodosuccinimide |
| NMR = | nuclear magnetic resonance |
| NTA = | nitrilotriacetic acid |
| NTP = | nucleotide triphosphate |
| RP HPLC = | reverse phase high performance liquid chromatography |
| s = | singlet |
| TBAF = | tetrabutylammonium fluoride |
| THF = | tetrahydrofuran |
| TFA = | trifluoroacetic acid |
| T$_m$ = | temperature of melting |
| μL = | microliters |
| v/v = | volume to volume |
| +wt % = | weight percent |
| μg = | micrograms |
| μM = | micromolar |

In addition, all reaction temperatures are in degrees Celcius unless reported otherwise and all percentages are molar percents again unless indicated otherwise.

Example 1

Preparation of the intermediate 1-O-methyl-2-methyl-3,5-bis-O-(2,4-dichlorobenzyl)-β-D-ribofuranose

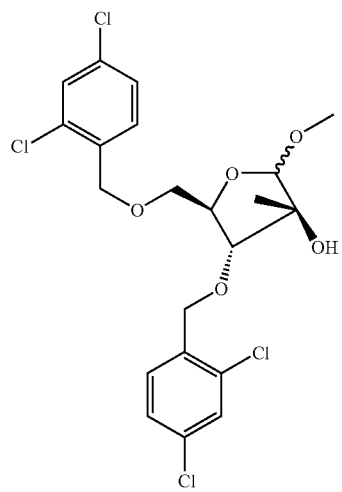

Step 1: Preparation of 1-O-methyl-2,3,5-tris-O-(2,4-dichlorobenzyl)-β-D-ribofuranose The title compound is synthesized using the methods described in Martin, P.; *Helv. Chim. Acta*, 1995, 78, 486 starting with commercially available D-ribose.

Step 2: Preparation of 1-O-methyl-3,5-bis-O-(2,4-dichlorobenzyl)-β-D-ribofuranose To a solution of the product of Step 1 (171.60 g, 0.2676 mol) in 1.8 L CH$_2$Cl$_2$ that was cooled to 0° C., was added dropwise a solution of stannous chloride (31.522 mL, 0.2676 mol) in 134 mL CH$_2$Cl$_2$ while stirring. After the solution was kept at 3° C. for 27 hours, another 5.031 ml of SnCl$_4$ (0.04282 mol) was added and the solution was kept at 3° C. overnight. After 43 hours the reaction was quenched by carefully adding the solution to 1.9 L saturated NaHCO$_3$ solution. Tin salts were removed via filtration through celite after which the organic phage was isolated, dried with MgSO$_4$ and evaporated in vacuo. The yield of raw, dark yellow oil was 173.6 g, which contains 2,4-dibenzoyl chloride. The crude oil was used directly in the next step without further purification.

Step 3: Preparation of 1-O-methyl-2-oxo-3,5-bis-O-(2,4-dichlorobenzyl)-β-D-ribofuranose To an ice-cold suspension of Dess-Martin periodinane (106.75 g, 0.2517 mol) in 740 mL anhydrous CH$_2$Cl$_2$, under argon, was added a solution of the product of Step 2 above in 662 mL anhydrous CH$_2$Cl$_2$ dropwise over 0.5 hours. The reaction mixture was stirred at 0° C. for 0.5 hours and then at room temperature for 6 days. The mixture was diluted with 1.26 L anhydrous Et$_2$O and poured into an ice-cold mixture of Na$_2$S$_2$O$_3$5H$_2$O (241.2 g, 1.5258 mol) in 4.7 L saturated aqueous NaHCO$_3$. The layers were separated, and the organic layer was washed with 1.3 L saturated aqueous NaHCO$_3$, 1.7 L water and 1.3 L brine, dried with MgSO$_4$, filtered and evaporated to give the target compound. This compound (72.38 g, 0.1507 mol) was used without further purification in the next step.

Step 4: Preparation of the Title Compound

A solution of MeMgBr in 500 mL anhydrous Et$_2$O at 55° C. was added dropwise to a solution of the product of Step 3 above (72.38 g, 0.1507 mol), also in 502 mL anhydrous Et$_2$O. The reaction mixture was allowed to warm to −30° C. and stirred mechanically for 4 hours at −30° C. to −15° C., then poured into 2 L ice cold water. After stirring vigorously at ambient temperature for 0.5 hours, the mixture was filtered through a Celite pad (14×5 cm), which was thoroughly washed with Et$_2$O. The organic layer was dried with MgSO$_4$, filtered and concentrated in vacuo. The residue was dissolved in hexanes (~1 mL per gram crude), applied to a silica gel column (1.5 L silica gel in hexanes) and eluted with hexanes and [4:1 hexanes:ethyl acetate, v/v] to give 53.58 g (0.1080 mol) of the final purified product. The morphology of the title compound was that of an off-yellow, viscous oil.
MS: m/z 514.06 (M+NH$_4$+).

Example 2

Preparation of 1-(6-Hydroxylamino-7-ethynyl-7-deazapurin-9-yl)-2-methyl-β-D-ribofuranose

Step 1: Synthesis of 6-Chloro-7-iodo-7-deazapurine:

6-Chloro-7-deazapurine 10.75 g (70 mmol) and N-iodosuccinimide (16.8 g, 75 mmol) were dissolved in 400 ml of dry DMF and left at ambient temperature in the darkness overnight. The solvent was evaporated. The dark residue was distributed between 500 ml of ethyl acetate and 150 ml of 10% Na$_2$SO$_3$. Organic fraction was washed with 10% Na$_2$SO$_3$ (2×100 ml), brine (150 ml), dried over Na$_2$SO$_4$ and evaporated. The yellow residue was crystallized from ethanol to yield 16.2 g (83%) of the title compound as off white crystals. The mother liquid was evaporated, dissolved in toluene, and purified by flush chromatography on silica gel (7×4 cm). The column was washed with toluene until the eluent was colorless than the title compound was eluted with 5% ethyl acetate in toluene to give additional 3.5 g of the title product.
Total yield is 98%.
T$_m$ 212-214 (dec)
UV λ$_{max}$: 307, 266, 230, 227 nm (methanol)
MS: 277.93 (M−H), 313 (M+Cl)
$^1$H-NMR (DMSO-d6): δ 12.94 (s, 1H, NH), 8.58 (s, 1H, H-2), 7.94 (s, 1H, H-8)

Step 2: Synthesis of 6-Chloro-7-trimethylsilanylethynyl-7-deazapurine:

The heterocycle obtained in Step 1 above (16 g, 64.25 mmol) was dried by co-evaporation with dry DMF (2×50 ml) and dissolved in DMF/THF mixture (800 ml, 1:3 v/v). Triethylamine (8.33 ml, 0.93 equiv.), CuI (4.9 g, 0.4 equiv.) and (trimethylsilyl) acetylene (54.5 ml, 6 equiv.) were added. The flask was filled with Ag then (Ph$_3$)$_4$Pd (7.4 g, 0.1 equiv.) was added and the mixture was left over night at ambient temperature. The solvent was evaporated; the dark residue was distributed between 1000 ml of ethyl acetate and 300 ml of water. Organic fraction was washed with brine (2×150 ml), dried over Na$_2$SO$_4$ and concentrated up to the volume 200 ml. Dry silica gel was added to the solution (about 400 ml) and the mixture was evaporated to dryness. The silica gel caring the reaction mixture was loaded onto the filter, containing silica gel in toluene (6×13 cm, about 1000 ml of silica gel). The filter was washed with toluene until the eluent was colorless; compound was eluted with toluene/ethyl acetate (9:1 v/v, 5 l). Solvent was evaporated and compound crystallized from acetone/hexane. The title compound was obtained by recrystallization from methanol. The 9.8 g of first crop was obtained as tan crystals; the second crop was 2.3 g, also tan crystals. Total yield 12.1 g (85%).
Tm 217-220 (dec)
UV λ$_{max}$: 311, 245, 239, 231 nm (methanol)
MS: 248.07 (M−H),
$^1$H-NMR (DMSO-d6): δ 12.92 (s, 1H, NH), 8.60 (s, 1H, H-2), 8.06 (s, 1H, H-8)

Step 3: Synthesis of 1-(6-Chloro-7-trimethylsilanylethynyl-7-deazapurin-9-yl)-2-methyl-3,5-di(-O-2,4-dichlorobenzyl)-β-D-ribofuranose:

The base, obtained as described in Step 2 above (9.8 g, 39 mmol) was suspended in 600 ml of CH$_3$CN, NaH was added (1.6 g, 39 mmol 60% in oil) and the reaction mixture was stirred at room temperature until the clear solution was formed (about 1 hour). 1-O-Methyl-2-methyl-3,5-di(-O-2,4-dichlorobenzyl)-β-D-ribofuranose (10 g, 20 mmol) was dissolved in 500 ml of DCM and cooled down to 4° C. in ice/water bath. HBr/AcOH (30 ml) was added dropwise, reaction mixture was kept in the bath for 1 hour more, solvents were evaporated and co-evaporated with dry toluene (2×50 ml), keeping all time the temperature below 25° C. The dark residue was dissolved in CH$_3$CN (100 ml) and added to the solution of Na-salt of the base. The reaction was kept overnight at ambient temperature. The solvent was evaporated and the dark residue was distributed between 1000 ml of ethyl acetate and 300 ml of 5% solution of citric acid. Organic fraction was washed with water (150 ml), brine (150 ml), dried over Na$_2$SO$_4$ and concentrated up to the volume 200 ml. Dry silica gel was added to the solution (about 400 ml) and the mixture was evaporated to dryness. The silica gel caring the reaction mixture was loaded onto the column (5×20 cm), packed in hexane. The column was washed with 10% EtOAc in hexane to elute first the side product-6-Chloro-7-trimethylsilanylethynyl-9-(2,4-dichlorobenzyl)-7-deazapurine; then the title compound was eluted. The elution was continued with 20% EtOAc/hexane to recover unreacted base as white crystals. The yield of the title compound 10.9 g, 76% as tan foam.

$^1$H-NMR (DMSO-d6): δ 8.75 (s, 1H, H-2), 8.20 (s, 1H, H-8), 7.63-7.38 (m, 6H, dichlorophenyl), 6.22 (s, 1H, H-1'), 5.65 (s, 1H, H-3'), 4.80-4.45 (m, 4H, CH$_2$-benzyl, 2'-OH, H-4'), 4.21 (s, 2H, CH$_2$-benzyl), 3.97 and 3.80 (dd, 1H, H-5'), 0.92 (s, 3H, 2'-methyl), 0.23 (s, 9H, Si(CH$_3$)$_3$)

Step 4: Synthesis of 1-(6-Chloro-7-trimethylsilanylethynyl-7-deazapurin-9-yl)-2-methyl-β-D-ribofuranose:

To the solution of the compound from the previous step (5.4 g, 7.5 mmol) in DCM (200 ml) at −78° C. was added boron trichloride (1M in DCM, 88 mL, 88 mmol) dropwise. The mixture was stirred at −78° C. for 2.5 hours band additionally 3 h at −20 to −30° C. The reaction was quenched by addition of methanol/DCM (90 mL, 1:1) and the resulting mixture stirred at −20° C. for 30 min, then neutralized by aqueous ammonia at the same temperature. The solid was filtered and washed with methanol/DCM (250 mL, 1:1). The combined filtrates were evaporated, and the residue was purified by chromatography on silica gel using for elution chloroform and then chloroform/methanol from 2% to 10% as step gradient. The desired compound was obtained as yellowish foam, the yield 2.2 g (75%).

$^1$H-NMR (DMSO-d6 δ.70 (s, 1H, H-2), 8.45 (s, 1H, H-8), 6.21 (s, 1H, H-1'), 5.40-5.20 (m, 3H, sugar), 4.00-3.60 (m, 4H, sugar), 0.84 (s, 3H, 2'-methyl), 0.23 (s, 9H, Si(CH$_3$)$_3$)

Step 5: Synthesis of 1-(6-hydroxylamino-7-ethynyl-7-deazapurin-9-yl)-2-methyl-β-D-ribofuranose:

Dry 6-chloro nucleoside from Step 4 above (300 mg, 1 mmol) was dissolved in dry ethanol, trimethylsilyl-O-hydroxylamine was added (300 mg) and reaction mixture was refluxed for 5 hours. Reaction was controlled by LC-MS. When no starting nucleoside was detected the mixture was cooled down to room temperature, neutralized with HCl/dioxane and evaporated to dryness. The residue was purified by RP HPLC 0% to 100% B in 20 min. A—0.05% TFA in water, B—0.05% TFA in acetonitrile, flow rate 10 ml/min. The first peak was collected and evaporated to dryness. The residue was dissolved in methanol, 200 ul of HCl/dioxane was added and solvents were evaporated. The residue was dissolved in 3 ml of methanol and precipitated by 35 ml of ether to yield 150 mg (50%) of the title compound as off-white powder.

MS: 321.11 (M+H)

$^1$H-NMR (DMSO-d6): δ 0.86 (s, 3H, CH3); 5.99 (s, 1H, H-1'); 7.88 and 7.92 (s, 1H, base).

Example 3

Preparation of 1-(6-hydroxylamino-7-ethenyl-7-deazapurin-9-yl)-2-methyl-β-D-ribofuranose

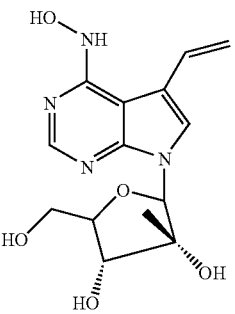

1-(6-Hydroxylamino-7-ethynyl-7-deazapurin-9-yl)-2-methyl-β-D-ribofuranose (Example 2) is dissolved in THF and placed under hydrogen (1 atm) in the presence of Lindlar's catalyst until one mole of hydrogen is consumed to provide the title compound.

BIOLOGICAL EXAMPLES

Example 1

Anti-Hepatitis C Activity

Compounds of this invention exhibit anti-hepatitis C activity by inhibiting HCV polymerase, by inhibiting other enzymes needed in the replication cycle, or by other pathways. A number of assays have been published to assess these activities. A general method that assesses the gross increase of HCV virus in culture is disclosed in U.S. Pat. No. 5,738,985 to Miles et al In vitro assays have been reported in Ferrari et al. *Jnl. of Vir.*, 73:1649-1654, 1999; Ishii et al., *Hepatology*, 29:1227-1235, 1999; Lohmann et al., *Jnl of Bio. Chem.*, 274:10807-10815, 1999; and Yamashita et al., *Jnl. of Bio. Chem.*, 273:15479-15486, 1998.

WO 97/12033, filed on Sep. 27, 1996, by Emory University, listing C. Hagedorn and A. Reinoldus as inventors, which claims priority to U.S. Ser. No. 60/004,383, filed on September 1995, describes an HCV polymerase assay that can be used to evaluate the activity of the of the compounds described herein. Another HCV polymerase assay has been reported by Bartholomeusz, et al., Hepatitis C Virus (HCV) RNA polymerase assay using cloned HCV non-structural proteins; Antiviral Therapy 1996:1(Supp 4) 18-24.

Screens that measure reductions in kinase activity from HCV drugs are disclosed in U.S. Pat. No. 6,030,785, to Katze et al., U.S. patent No. Delvecchio et al., and U.S. Pat. No. 5,759,795 to Jubin et al. Screens that measure the protease inhibiting activity of candidate HCV drugs are disclosed in U.S. Pat. No. 5,861,267 to Su et al, U.S. Pat. No. 5,739,002 to De Francesco et al., and U.S. Pat. No. 5,597,691 to Houghton et al.

Example 2

Replicon Assay

A cell line, ET (Huh-lucubineo-ET) was used for screening of compounds of the present invention for HCV RNA dependent RNA polymerase. The ET cell line was stably transfected with RNA transcripts harboring a $I_{389}$luc-ubi-neo/NS3-3'/ET; replicon with firefly luciferase-ubiquitin-neomycin phosphotransferase fusion protein and EMCV-IRES driven NS3-5B polyprotein containing the cell culture adaptive mutations (E1202G; T1280I; K1846T) (Krieger at al, 2001 and unpublished). The ET cells were grown in DMEM, supplemented with 10% fetal calf serum, 2 mM Glutamine, Penicillin (100 IU/mL)/Streptomycin (100 µg/ml), 1× nonessential amino acids, and 250 µg/mL G418 ("Geneticin"). They are all available through Life Technologies (Bethesda, Md.). The cells were plated at 0.5-1.0×10$^4$ cells/well in the 96 well plates and incubated for 24 h before adding nucleoside analogs. Then the compounds each at 5 and 50 µM were added to the cells. Luciferase activity was measured 48-72 hours later by adding a lysis buffer and the substrate (Catalog number Glo-lysis buffer E2661 and Bright-Glo luciferase system E2620 Promega, Madison, Wis.). Cells should not be too confluent during the assay. Percent inhibition of replication was plotted relative to no compound control. Under the same condition, cytotoxicity of the compounds was determined using cell proliferation reagent, WST-1 (Roche, Germany). The compounds showing antiviral activities, but no significant cytotoxicities are chosen to determine $IC_{50}$ and $TC_{50}$.

Example 3

Cloning and Expression of Recombinant HCV-NS5b

The coding sequence of NS5b protein was cloned by PCR from pFKI$_{389}$luc/NS3-3'/ET as described by Lohmann, V., et al. (1999) *Science* 285, 110-113 using the following primers:

aggacatggatccgcggggtcgggcacgagacag (SEQ. ID. NO. 1)
aaggctggcatgcactcaatgtcctacacatggac (SEQ. ID. NO. 2)

The cloned fragment was missing the C terminus 21 amino acid residues. The cloned fragment was inserted into an IPTG-inducible expression plasmid that provides an epitope tag (His)6 at the carboxy terminus of the protein.

The recombinant enzyme was expressed in XL-1 cells and after induction of expression, the protein was purified using affinity chromatography on a nickel-NTA column. Storage condition is 10 mM Tris-HCl pH 7.5, 50 mM NaCl, 0.1 mM EDTA, 1 mM DTT, 20% glycerol at −20° C.

Example 4

HCV-NS5b Enzyme Assay

The polymerase activity is assayed by measuring incorporation of radiolabeled UTP into a RNA product using a poly-A template (1000-10000 nucleotides) and oligo-U$_{12}$ primer. Alternatively, a portion of the HCV genome is used as template and radiolabeled GTP is used. Typically, the assay mixture (50 µL) contains 10 mM Tris-HCl (pH7.5), 5 mM MgCl$_2$, 0.2 mM EDTA, 10 mM KCl, 1 unit/µL RNAsin, 1 mM DTT, 10 µM each of NTP, alpha-[$^{32}$P]-GTP, 10 ng/µL polyA template and 1 ng/µL oligoU primer. Test compounds are dissolved in water containing 0 to 1% DMSO. Typically, compounds are tested at concentrations between 1 nM and 100 µM. Reactions are started with addition of enzyme and allowed to continue at room temperature or 30° C. for 1 to 2 h. Reactions are quenched with 20 µL 10 mM EDTA and reaction mixtures (50 µL) spotted on DE81 filter disc to capture the radiolabelled RNA products. After washing with 0.5 mM Na$_2$HPO$_4$ (3 times), water (1 time) and ethanol (1 time) to remove unincorporated NTP, the discs are dried and the incorporation of radioactivity is determined by scintillation counting.

FORMULATION EXAMPLES

The following are representative pharmaceutical formulations containing a compound of Formula IV or IVA.

Example 1

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Example 2

Capsule Formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Example 3

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| Sorbitol (70% solution) | 13.00 g |
| Veegum K (Vanderbilt Co.) | 1.0 g |
| flavoring | 0.035 ml |
| colorings | 0.5 mg |
| distilled water | q.s. to 100 ml |

Example 4

Injectable Formulation

The following ingredients are mixed to form an injectable formulation.

| Ingredient | Amount |
| --- | --- |
| compound of this invention | 0.2 mg-20 mg |
| sodium acetate buffer solution, 0.4 M | 2.0 ml |
| HCl (1N) or NaOH (1N) | q.s. to suitable pH |
| water (distilled, sterile) | q.s. to 20 ml |

Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Amount |
| --- | --- |
| compound of the invention | 500 mg |
| Witepsol ® H-15 | balance |

From the foregoing description, various modifications and changes in the above described invention will occur to those skilled in the art. All such modifications coming within the scope of the appended claims are intended to be included therein.

What is claimed is:

1. A method for treating a hepatitis C viral infection in mammals which method comprises administering to a mammal that has been diagnosed with said viral infection a compound of Formula I below:

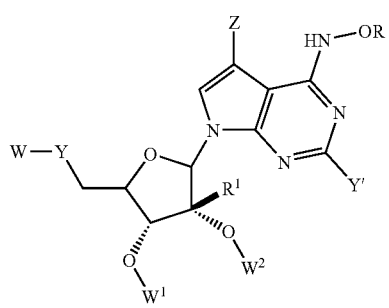

wherein:
W is selected from the group consisting of hydrogen, monophosphate, diphosphate, and triphosphate;
$W^1$ is hydrogen or acyl;
$W^2$ is hydrogen or acyl;
R is selected from the group consisting of hydrogen or $(C_1-C_3)$alkyl;
$R^1$ is selected from the group consisting of hydrogen, alkyl, substituted alkyl, alkenyl, substituted alkenyl, alkynyl and substituted alkynyl;
Y is a bond, —$CH_2$— or —O—;
Y' is selected from the group consisting of hydrogen, halo, hydroxyl, thioalkyl, amino and substituted amino;
Z is selected from the group consisting of formyl, —B(OH)$_2$, nitro, alkenyl, substituted alkenyl, acetylenyl and substituted acetylenyl of the formula —C≡C—$R^4$;
$R^4$ is selected from the group consisting of phenyl, substituted phenyl, heteroaryl, substituted heteroaryl, —Si$(R^8)_3$, carboxyl, carboxyl esters, and —C(O)NR$^6$R$^7$ where $R^6$ and $R^7$ are independently hydrogen, alkyl or $R^6$ and $R^7$ together with the nitrogen atom pendent thereto are joined to form a heterocyclic, substituted heterocyclic, heteroaryl or substituted heteroaryl group; and
each $R^8$ is independently $(C_1-C_4)$alkyl or phenyl;
or pharmaceutically acceptable salts thereof;
wherein
substituted alkyl refers to an alkyl group having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic;
alkoxy refers to alkyl-O—;
substituted alkoxy refers to (substituted alkyl)-O—;
acyl refers to a moiety selected from the group consisting of H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)— and substituted heterocyclic-C(O)—;
acylamino refers to —C(O)NR$^{10}$R$^{10}$ where each $R^{10}$ independently is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each $R^{10}$ is joined to form together with the nitrogen atom a heterocyclic or substituted heterocyclic ring;
acyloxy refers to a moiety selected from the group consisting of alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—;
substituted alkenyl refers to an alkenyl group having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic with the proviso that any hydroxyl substitution is not attached to a vinyl (unsaturated) carbon atom;
substituted alkynyl refers to an alkynyl group having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic;
amino refers to —$NH_2$;
substituted amino refers to —NR'R", where R' and R" independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic or substituted heterocyclic group provided that R' and R" are both not hydrogen;
aminoacyl refers to a moiety selected from the group consisting of —NR$^{11}$C(O)alkyl, —NR$^{11}$C(O)substituted alkyl, —NR$^{11}$C(O)cycloalkyl, —NR$^{11}$C(O)substituted cycloalkyl, —NR$^{11}$C(O)alkenyl, —NR$^{11}$C(O)substituted alkenyl, —NR$^{11}$C(O)alkynyl, —NR$^{11}$C(O)substituted alkynyl, —NR$^{11}$C(O)aryl, —NR$^{11}$C(O)substituted aryl, —NR$^{11}$C(O)heteroaryl, —NR$^{11}$C(O)substituted heteroaryl, —NR$^{11}$C(O)heterocyclic, and —NR$^{11}$C(O)substituted heterocyclic where $R^{11}$ is hydrogen or alkyl;
aryl refers to a monovalent aromatic carbocyclic group of from 6 to 14 carbon atoms having a single ring or multiple condensed rings, which condensed rings may or may not be aromatic, provided that the point of attachment is at an aromatic carbon atom;
substituted aryl refers to an aryl group substituted with from 1 to 3 substituents selected from the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy;

aryloxy refers to aryl-O—;

substituted aryloxy refers to (substituted aryl)-O—;

carboxyl refers to —COOH or salts thereof;

carboxyl ester refers to a moiety selected from the group consisting of —C(O)O-alkyl, —C(O)O-substituted alkyl, —C(O)Oaryl, and —C(O)O-substituted aryl;

cycloalkyl refers to a cyclic alkyl group of from 3 to 10 carbon atoms having single or multiple cyclic rings;

substituted cycloalkyl refers to an cycloalkyl group, having from 1 to 5 substituents selected from the group consisting of oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic;

cycloalkoxy refers to —O-cycloalkyl;

substituted cycloalkoxy refers to —O-(substituted cycloalkyl);

halogen refers to fluoro, chloro, bromo or iodo;

heteroaryl refers to an aromatic group of from 1 to 10 carbon atoms and 1 to 4 heteroatoms selected from the group consisting of oxygen, nitrogen, sulfur, —S(O)—, and —S(O)$_2$— within the ring, wherein the heteroaryl group can have a single ring or multiple condensed rings wherein the condensed rings may or may not be aromatic and/or contain a heteroatom provided that the point of attachment is through an atom of the aromatic heteroaryl group;

substituted heteroaryl refers to a heteroaryl group substituted with from 1 to 3 substituents selected from the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy;

heteroaryloxy refers to —O-heteroaryl;

substituted heteroaryloxy refers to —O-(substituted heteroaryl);

heterocyclyl refers to a saturated or unsaturated, but not heteroaromatic, group having a single ring or multiple condensed rings, from 1 to 10 carbon atoms and from 1 to 4 hetero atoms selected from the group consisting of nitrogen, oxygen, sulfur, —S(O)— and —S(O)$_2$— within the ring wherein, in fused ring systems, one or more the rings can be cycloalkyl, aryl or heteroaryl provided that the point of attachment is through the heterocyclic ring;

substituted heterocyclyl refers to a heterocyclyl substituted with from 1 to 3 substituents selected from the group consisting of oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic;

heterocyclyloxy refers to —O-heterocyclic;

substituted heterocyclyloxy refers to —O-(substituted heterocyclic);

phosphate refers to a moiety selected from the group consisting of —P(O)(OH)$_2$ (monophosphate), —P(O)(OH)OP(O)(OH)$_2$ (diphosphate) and —P(O)(OH)OP(O)(OH)OP(O)(OH)$_2$ (triphosphate) or salts thereof including partial salts thereof;

phosphonate refers to a moiety selected from the group consisting of —P(O)(R$^{12}$)(OH) or —P(O)(R$^{12}$)(OR$^{13}$) or salts thereof including partial salts thereof, wherein each R$^{12}$ is independently selected from hydrogen, alkyl, substituted alkyl, carboxylic acid, and carboxyl ester and R$^{13}$ is alkyl or substituted alkyl;

sulfonate ester refers to —SO$_2$OR$^{14}$ where R$^{14}$ is selected from the group consisting of alkyl, substituted alkyl, alkenyl, substituted alkenyl, aryl, substituted aryl, heteroaryl, substituted heteroaryl, heterocyclic and substituted heterocyclic;

and wherein thiol refers to —SH;

thioalkyl refers to —S-alkyl;

substituted thioalkyl refers to —S-(substituted alkyl);

thiocycloalkyl refers to —S-cycloalkyl;

substituted thiocycloalkyl refers to —S-(substituted cycloalkyl);

thioaryl refers to —S-aryl;

substituted thioaryl refers to —S-(substituted aryl);

thioheteroaryl refers to —S-heteroaryl;

substituted thioheteroaryl refers to —S-(substituted heteroaryl);

thioheterocyclic refers to —S-heterocyclic; and substituted thioheterocyclic refers to —S-(substituted heterocyclic).

2. The method of claim 1, wherein one of W$^1$ and W$^2$ is an acyl group selected from the group consisting of acetyl, trimethylacetyl, and acyl groups derived from amino acids.

3. The method of claim 1 wherein, Z is selected from the group consisting of formyl, nitro, acetylenyl and substituted acetylenyl of the formula —C≡C—R$^4$ where R$^4$ is as defined above.

4. The method of claim 3 wherein, Z is selected from formyl, nitro, and —C≡C—R$^4$ and R$^4$ is selected from phenyl, and —Si(CH$_3$)$_3$.

5. The method of claim 1 wherein the compound of Formula I is selected from the group consisting of:
  1-(6-hydroxylamino-7-ethynyl-7-deazapurin-9-yl)-2-methyl-β-D-ribofuranose (1);
  1-(6-hydroxylamino-7-(2-phenylethyn-1-yl)-7-deazapurin-9-yl)-2-methyl-β-D-ribofuranose (2);
  1-(6-hydroxylamino-7-(2-(pyridin-2-yl)-ethyn-1-yl)-7-deazapurin-9-yl)-2-methyl-β-D-ribofuranose (3);
  1-(6-hydroxylamino-7-(2-(4-fluorophenyl)ethyn-1-yl)-7-deazapurin-9-yl)-2-methyl-β-D-ribofuranose (4);

1-(6-hydroxylamino-7-(2-(4-methylphenyl)ethyn-1-yl)-7-deaza-purin-9-yl)-2-methyl-β-D-ribofuranose (5);
1-(6-hydroxylamino-7-(2-carboxylethyn-1-yl)-7-deazapurin-9-yl)-2-methyl-β-D-ribofuranose (6);
1-(6-hydroxylamino-7-(2-ethyl carboxylethyn-1-yl)-7-deazapurin-9-yl)-2-methyl-β-D-ribofuranose (7);
1-(6-hydroxylamino-7-(2-carboxamidoethyn-1-yl)-7-deazapurin-9-yl)-2-methyl-β-D-ribofuranose (8);
1-(6-hydroxylamino-7-(2-trimethylsilylethyn-1-yl)-7-deazapurin-9-yl)-2-methyl-β-D-ribofuranose (9);
1-(6-hydroxylamino-7-ethenyl-7-deaza-purin-9-yl)-2-methyl-β-D-ribofuranose (10);
1-(6-hydroxylamino-7-formyl-7-deaza-purin-9-yl)-2-methyl-β-D-ribofuranose (11);
1-(6-hydroxylamino-7-(boronic acid)-7-deazapurin-9-yl)-2-methyl-β-D-ribofuranose (13);
1-(6-hydroxylamino-7-(2,2-difluorovinyl)-7-deazapurin-9-yl)-2-methyl-β-D-ribofuranose (14);
1-(6-hydroxylamino-7-(2-cis-methoxyvinyl)-7-deazapurin-9-yl)-2-methyl-β-D-ribofuranose (15);
1-(6-hydroxylamino-7-nitro-7-deaza-purin-9-yl)-2-methyl-β-D-ribofuranose (16);
1-(6-methoxyamino-7-ethynyl-7-deazapurin-9-yl)-2-methyl-β-D-ribofuranose (18);
1-(6-methoxyamino-7-nitro-7-deaza-purin-9-yl)-2-methyl-β-D-ribofuranose (19); and
1-(6-methoxyamino-7-formyl-7-deaza-purin-9-yl)-2-methyl-β-D-ribofuranose (20);
and pharmaceutically acceptable salts thereof.

\* \* \* \* \*

```
                          SEQUENCE LISTING

<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aggacatgga tccgcggggt cgggcacgag acag                                   34

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaggctggca tgcactcaat gtcctacaca tggac                                  35
```